US009259142B2

(12) United States Patent
Jacobsen et al.

(10) Patent No.: US 9,259,142 B2
(45) Date of Patent: *Feb. 16, 2016

(54) METHOD AND DEVICE FOR INCREMENTAL WAVELENGTH VARIATION TO ANALYZE TISSUE

(71) Applicant: Sarcos LC, Salt Lake City, UT (US)

(72) Inventors: Stephen C. Jacobsen, Waltham, MA (US); Fraser M. Smith, Waltham, MA (US); David P. Marceau, Waltham, MA (US)

(73) Assignee: Sarcos LC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/940,791

(22) Filed: Jul. 12, 2013

(65) Prior Publication Data

US 2014/0022366 A1    Jan. 23, 2014

Related U.S. Application Data

(63) Continuation of application No. 12/512,188, filed on Jul. 30, 2009, now Pat. No. 8,486,735.

(60) Provisional application No. 61/084,755, filed on Jul. 30, 2008.

(51) Int. Cl.
*A61B 1/04* (2006.01)
*H04N 5/64* (2006.01)
(Continued)

(52) U.S. Cl.
CPC ............... *A61B 1/06* (2013.01); *A61B 1/00188* (2013.01); *A61B 1/05* (2013.01); *A61B 1/051* (2013.01);
(Continued)

(58) Field of Classification Search
CPC ..................................................... G01N 21/255
USPC ....... 438/29; 348/45, 744; 356/364; 600/109, 600/117, 466
See application file for complete search history.

(56) References Cited

U.S. PATENT DOCUMENTS 3,787,121 A * 1/1974 Lowy et al. ..................... 356/73
3,817,635 A   6/1974 Kawahara
(Continued)

FOREIGN PATENT DOCUMENTS

CN       1481753       3/2004
DE    197 42 973       4/1998
(Continued)

OTHER PUBLICATIONS

Boppart, S.A. et al., "Forward-imaging instruments for optical coherence tomography." Optics Letters, Nov. 1, 1997, vol. 22, No. 21, pp. 1618-1620.
(Continued)

*Primary Examiner* — Viet Vu
*Assistant Examiner* — Michael A Chambers
(74) *Attorney, Agent, or Firm* — Thorpe North & Western, LLP

(57) ABSTRACT

A method of imaging a target using a miniaturized imaging device is disclosed comprising providing a miniaturized imaging device having a stationary lens system and an imaging array, wherein the distance from a distal end of the stationary lens system to the imaging array is fixed. The miniaturized imaging device is advanced near the desired target and a distance from a distal end of the stationary lens system to the desired target is determined. A desired wavelength of light is calculated based on the determined distance from the distal end of the stationary lens system to the desired target and the desired wavelength of light is propagated onto the target.

20 Claims, 5 Drawing Sheets

(51) Int. Cl.
  *A61B 8/14* (2006.01)
  *A61B 1/06* (2006.01)
  *A61B 1/00* (2006.01)
  *A61B 1/05* (2006.01)
  *G01N 21/25* (2006.01)

(52) U.S. Cl.
  CPC ............ *A61B 1/0638* (2013.01); *A61B 1/0676* (2013.01); *A61B 1/0684* (2013.01); *G01N 21/255* (2013.01)

(56) References Cited

U.S. PATENT DOCUMENTS

| | | |
|---|---|---|
| 3,856,000 A | 12/1974 | Chikama |
| 3,886,933 A | 6/1975 | Mori et al. |
| 3,918,438 A | 11/1975 | Hayamizu et al. |
| 3,971,065 A | 7/1976 | Bayer |
| 4,277,168 A | 7/1981 | Oku |
| 4,283,115 A | 8/1981 | Fraissl |
| 4,349,456 A | 9/1982 | Sowman |
| 4,360,275 A | 11/1982 | Louderback |
| 4,403,985 A | 9/1983 | Boretos |
| 4,475,902 A | 10/1984 | Schubert |
| 4,487,206 A | 12/1984 | Aagard |
| 4,491,865 A | 1/1985 | Danna et al. |
| 4,515,444 A | 5/1985 | Prescott et al. |
| 4,521,284 A | 6/1985 | Tanabe et al. |
| 4,573,450 A | 3/1986 | Arakawa |
| 4,585,349 A | 4/1986 | Gross et al. |
| 4,589,404 A | 5/1986 | Barath et al. |
| 4,593,313 A * | 6/1986 | Nagasaki et al. ............... 348/70 |
| 4,594,613 A | 6/1986 | Shinbori et al. |
| 4,600,831 A | 7/1986 | Hutley |
| 4,604,992 A | 8/1986 | Sato |
| 4,620,534 A | 11/1986 | Zartman |
| 4,621,284 A * | 11/1986 | Nishioka et al. ............... 348/69 |
| 4,622,954 A | 11/1986 | Arakawa et al. |
| 4,626,079 A | 12/1986 | Nakamura et al. |
| 4,641,927 A | 2/1987 | Prescott et al. |
| 4,646,724 A | 3/1987 | Sato et al. |
| 4,672,218 A | 6/1987 | Chrisman et al. |
| 4,706,118 A | 11/1987 | Kato et al. |
| 4,707,134 A | 11/1987 | McLachlan et al. |
| 4,723,843 A | 2/1988 | Zobel |
| 4,725,721 A | 2/1988 | Nakamura |
| 4,745,470 A | 5/1988 | Yabe et al. |
| 4,745,471 A | 5/1988 | Takamura et al. |
| 4,783,591 A | 11/1988 | Sullivan |
| 4,785,815 A | 11/1988 | Cohen |
| 4,790,624 A | 12/1988 | Van Hoye et al. |
| 4,791,479 A | 12/1988 | Ogiu et al. |
| 4,802,487 A | 2/1989 | Martin et al. |
| 4,803,562 A | 2/1989 | Eino |
| 4,832,003 A | 5/1989 | Yabe |
| 4,843,416 A | 6/1989 | Brower |
| 4,846,785 A | 7/1989 | Cassou et al. |
| 4,859,040 A | 8/1989 | Kitagishi et al. |
| 4,867,137 A | 9/1989 | Takahashi |
| 4,867,138 A | 9/1989 | Kubota et al. |
| 4,867,174 A | 9/1989 | Skribiski |
| 4,880,298 A | 11/1989 | Takada |
| 4,895,138 A | 1/1990 | Yabe |
| 4,926,257 A | 5/1990 | Miyazaki |
| 4,930,880 A | 6/1990 | Miyauchi |
| 4,932,394 A | 6/1990 | Nanaumi |
| 4,934,340 A | 6/1990 | Ebling et al. |
| 4,941,457 A | 7/1990 | Hasegawa |
| 4,998,807 A | 3/1991 | Uzawa et al. |
| 5,006,928 A | 4/1991 | Kawajiri et al. |
| 5,009,483 A | 4/1991 | Rockwell, III |
| 5,021,888 A | 6/1991 | Kondou et al. |
| 5,022,972 A | 6/1991 | David et al. |
| 5,032,913 A * | 7/1991 | Hattori et al. .................. 348/70 |
| 5,040,069 A | 8/1991 | Matsumoto et al. |
| 5,061,036 A | 10/1991 | Gordon |
| 5,093,719 A | 3/1992 | Prescott |
| 5,105,269 A * | 4/1992 | Nakamura et al. ............ 348/162 |
| 5,106,387 A | 4/1992 | Kittrell et al. |
| 5,109,859 A | 5/1992 | Jenkins |
| 5,111,804 A | 5/1992 | Funakoshi |
| 5,113,254 A | 5/1992 | Kanno et al. |
| 5,121,213 A | 6/1992 | Nishioka |
| 5,126,369 A | 6/1992 | Wilson et al. |
| 5,126,639 A * | 6/1992 | Srivastava ..................... 315/364 |
| 5,130,804 A | 7/1992 | Tamura et al. |
| 5,165,063 A | 11/1992 | Strater et al. |
| 5,166,656 A | 11/1992 | Badihi et al. |
| 5,182,672 A | 1/1993 | Mukai et al. |
| 5,188,093 A | 2/1993 | Lafferty et al. |
| 5,190,523 A | 3/1993 | Lindmayer |
| 5,191,203 A | 3/1993 | McKinley |
| 5,198,894 A | 3/1993 | Hicks |
| 5,209,219 A | 5/1993 | Hollobaugh |
| 5,220,198 A | 6/1993 | Tsuji |
| 5,222,477 A | 6/1993 | Lia |
| 5,228,430 A | 7/1993 | Sakamoto |
| 5,258,834 A | 11/1993 | Tsuji et al. |
| 5,289,434 A | 2/1994 | Berni |
| 5,290,555 A | 3/1994 | Guthauser et al. |
| 5,291,010 A | 3/1994 | Tsuji |
| 5,298,741 A | 3/1994 | Walt et al. |
| 5,304,173 A | 4/1994 | Kittrell et al. |
| 5,305,098 A | 4/1994 | Matsunaka et al. |
| 5,318,024 A | 6/1994 | Kittrell et al. |
| 5,361,166 A | 11/1994 | Atkinson et al. |
| 5,365,268 A | 11/1994 | Minami |
| 5,376,960 A | 12/1994 | Wurster |
| 5,377,047 A | 12/1994 | Broome et al. |
| 5,381,784 A | 1/1995 | Adair |
| 5,396,366 A | 3/1995 | Brown et al. |
| 5,398,685 A | 3/1995 | Wilk et al. |
| 5,402,769 A | 4/1995 | Tsuji |
| 5,408,999 A | 4/1995 | Singh et al. |
| 5,430,475 A | 7/1995 | Goto et al. |
| 5,434,615 A | 7/1995 | Matumoto |
| 5,436,655 A | 7/1995 | Hiyama et al. |
| 5,438,975 A | 8/1995 | Miyagi et al. |
| 5,440,669 A | 8/1995 | Rakuljic et al. |
| 5,450,243 A * | 9/1995 | Nishioka ....................... 359/710 |
| 5,455,455 A | 10/1995 | Badehi |
| 5,458,612 A | 10/1995 | Chin |
| 5,459,570 A | 10/1995 | Swanson et al. |
| 5,469,841 A | 11/1995 | Kobayashi et al. |
| 5,494,483 A | 2/1996 | Adair |
| 5,512,940 A | 4/1996 | Takasugi et al. |
| 5,517,997 A | 5/1996 | Fontenot |
| 5,531,664 A | 7/1996 | Adachi et al. |
| 5,547,455 A | 8/1996 | McKenna |
| 5,547,906 A | 8/1996 | Badehi |
| 5,594,497 A | 1/1997 | Ahern |
| 5,603,687 A | 2/1997 | Hori et al. |
| 5,607,435 A | 3/1997 | Sachdeva et al. |
| 5,621,574 A | 4/1997 | Foo |
| 5,630,788 A | 5/1997 | Forkner et al. |
| 5,647,368 A | 7/1997 | Zeng et al. |
| 5,662,621 A | 9/1997 | Lafontaine |
| 5,673,083 A | 9/1997 | Izumi et al. |
| 5,685,311 A | 11/1997 | Hara |
| 5,693,043 A | 12/1997 | Kittrell et al. |
| 5,704,892 A | 1/1998 | Adair |
| 5,716,323 A | 2/1998 | Lee |
| 5,716,759 A | 2/1998 | Badehi |
| 5,722,403 A | 3/1998 | McGee et al. |
| 5,732,150 A | 3/1998 | Zhou et al. |
| 5,740,808 A | 4/1998 | Panescu et al. |
| 5,749,827 A | 5/1998 | Minami |
| 5,751,340 A | 5/1998 | Strobl et al. |
| 5,752,518 A | 5/1998 | McGee et al. |
| 5,769,792 A | 6/1998 | Palcic et al. |
| 5,772,597 A | 6/1998 | Goldberger et al. |
| 5,776,049 A | 7/1998 | Takahashi |
| 5,783,829 A | 7/1998 | Sealock et al. |
| 5,784,098 A * | 7/1998 | Shoji et al. ..................... 348/45 |
| 5,792,984 A | 8/1998 | Bloom |

(56) References Cited

U.S. PATENT DOCUMENTS

| | | |
|---|---|---|
| 5,800,341 A | 9/1998 | McKenna et al. |
| 5,807,261 A | 9/1998 | Benaron et al. |
| 5,808,665 A | 9/1998 | Green |
| 5,818,644 A | 10/1998 | Noda |
| 5,827,172 A | 10/1998 | Takahashi et al. |
| 5,827,531 A | 10/1998 | Morrison et al. |
| 5,840,017 A | 11/1998 | Furusawa et al. |
| 5,846,185 A | 12/1998 | Carollo |
| 5,848,969 A | 12/1998 | Panescu et al. |
| 5,865,729 A | 2/1999 | Meehan et al. |
| 5,870,229 A | 2/1999 | Tsuchida |
| 5,873,816 A | 2/1999 | Kagawa et al. |
| 5,879,285 A | 3/1999 | Ishii |
| 5,904,651 A | 5/1999 | Swanson et al. |
| 5,908,445 A | 6/1999 | Whayne et al. |
| 5,913,817 A | 6/1999 | Lee |
| 5,916,155 A | 6/1999 | Levinson et al. |
| 5,929,900 A | 7/1999 | Yamanaka et al. |
| 5,940,126 A | 8/1999 | Kimura |
| 5,947,894 A | 9/1999 | Chapman et al. |
| 5,951,462 A | 9/1999 | Yamanaka |
| 5,957,849 A | 9/1999 | Munro |
| 5,971,915 A | 10/1999 | Yamamoto et al. |
| 5,973,779 A | 10/1999 | Ansari et al. |
| 5,980,663 A | 11/1999 | Badehi |
| 5,998,878 A | 12/1999 | Johnson |
| 5,999,327 A | 12/1999 | Nagaoka |
| 6,008,123 A | 12/1999 | Kook et al. |
| 6,014,919 A | 1/2000 | Jacobsen et al. |
| 6,022,758 A | 2/2000 | Badehi |
| 6,040,235 A | 3/2000 | Badehi |
| 6,059,760 A | 5/2000 | Sandmore et al. |
| 6,095,970 A | 8/2000 | Hidaka et al. |
| 6,117,707 A | 9/2000 | Badehi |
| 6,118,476 A | 9/2000 | Morito et al. |
| 6,133,637 A | 10/2000 | Hikita et al. |
| 6,134,003 A | 10/2000 | Tearney et al. |
| 6,139,489 A | 10/2000 | Wampler et al. |
| 6,139,819 A | 10/2000 | Unger et al. |
| 6,142,930 A | 11/2000 | Ito et al. |
| 6,161,035 A | 12/2000 | Furusawa |
| 6,184,923 B1 | 2/2001 | Miyazaki |
| 6,193,908 B1 | 2/2001 | Hampden-Smith et al. |
| 6,211,955 B1 | 4/2001 | Basiji et al. |
| 6,224,969 B1 | 5/2001 | Steenbergen et al. |
| 6,261,226 B1 | 7/2001 | McKenna et al. |
| 6,262,855 B1 | 7/2001 | Greisz |
| 6,271,206 B1 | 8/2001 | Pillai et al. |
| 6,280,960 B1 | 8/2001 | Carr |
| 6,288,172 B1 | 9/2001 | Goetz et al. |
| 6,319,745 B1 | 11/2001 | Bertin et al. |
| 6,322,498 B1 | 11/2001 | Gravenstein et al. |
| 6,327,096 B1 | 12/2001 | Tsuchida |
| 6,352,503 B1 | 3/2002 | Matsui |
| 6,361,491 B1 | 3/2002 | Hasegawa et al. |
| 6,366,726 B1 | 4/2002 | Wach et al. |
| 6,375,635 B1 | 4/2002 | Moutafis et al. |
| 6,384,397 B1 | 5/2002 | Takiar et al. |
| 6,384,884 B1 | 5/2002 | Nakamura et al. |
| 6,396,116 B1 | 5/2002 | Kelly et al. |
| 6,407,768 B1 | 6/2002 | Ishikawa |
| 6,445,939 B1 | 9/2002 | Swanson et al. |
| 6,456,423 B1 | 9/2002 | Nayfeh et al. |
| 6,471,363 B1 | 10/2002 | Howell et al. |
| 6,485,413 B1 | 11/2002 | Boppart et al. |
| 6,522,913 B2 | 2/2003 | Panescu et al. |
| 6,525,866 B1 | 2/2003 | Lin et al. |
| 6,533,722 B2 | 3/2003 | Nakashima |
| 6,537,205 B1 | 3/2003 | Smith |
| 6,551,302 B1 | 4/2003 | Rosinko et al. |
| 6,552,796 B2 | 4/2003 | Magnin et al. |
| 6,561,972 B2 | 5/2003 | Ooshima et al. |
| 6,570,659 B2 | 5/2003 | Schmitt |
| 6,573,950 B1 * | 6/2003 | Hirata et al. ............ 348/744 |
| 6,585,717 B1 | 7/2003 | Wittenberger et al. |
| 6,595,913 B2 | 7/2003 | Takahashi |
| 6,618,614 B1 | 9/2003 | Chance et al. |
| 6,622,367 B1 | 9/2003 | Bolduc et al. |
| 6,643,071 B2 | 11/2003 | Schnitzer |
| 6,658,279 B2 | 12/2003 | Swanson et al. |
| 6,659,941 B2 | 12/2003 | Weber et al. |
| 6,695,787 B2 | 2/2004 | Hogendijk et al. |
| 6,710,919 B1 | 3/2004 | Clausen |
| 6,719,686 B2 | 4/2004 | Coakley et al. |
| 6,727,313 B2 | 4/2004 | Zhou et al. |
| 6,756,437 B1 | 6/2004 | Xue et al. |
| 6,761,684 B1 | 7/2004 | Speier |
| 6,785,048 B2 | 8/2004 | Yamaguchi et al. |
| 6,826,422 B1 | 11/2004 | Modell et al. |
| 6,827,683 B2 | 12/2004 | Otawara |
| 6,833,916 B2 | 12/2004 | Osipchuk et al. |
| 6,834,158 B1 | 12/2004 | Templeton |
| 6,842,288 B1 | 1/2005 | Liu et al. |
| 6,850,659 B2 | 2/2005 | Han |
| 6,879,851 B2 | 4/2005 | McNamara et al. |
| 6,881,448 B1 | 4/2005 | Hattori |
| 6,891,984 B2 | 5/2005 | Petersen et al. |
| 6,893,432 B2 | 5/2005 | Intintoli et al. |
| 6,894,729 B2 * | 5/2005 | Hirata et al. ............ 348/744 |
| 6,898,458 B2 | 5/2005 | Zeng et al. |
| 6,900,913 B2 | 5/2005 | Chen |
| 6,930,705 B2 | 8/2005 | Tanaka |
| 6,937,268 B2 | 8/2005 | Ogawa |
| 6,939,348 B2 | 9/2005 | Malecki et al. |
| 6,941,041 B2 * | 9/2005 | Yamaguchi et al. ........ 385/34 |
| 6,944,204 B2 | 9/2005 | Zhou et al. |
| 6,953,432 B2 | 10/2005 | Schiefer |
| 6,956,624 B2 * | 10/2005 | Hirata et al. ............ 348/744 |
| 6,960,165 B2 | 11/2005 | Ueno et al. |
| 6,982,740 B2 | 1/2006 | Adair et al. |
| 6,990,271 B2 | 1/2006 | Gafsi et al. |
| 7,030,904 B2 | 4/2006 | Adair et al. |
| 7,033,317 B2 | 4/2006 | Pruitt |
| 7,058,294 B2 | 6/2006 | Nakahara |
| 7,075,576 B2 | 7/2006 | Creasey et al. |
| 7,081,927 B2 * | 7/2006 | Hirata et al. ............ 348/744 |
| 7,091,500 B2 | 8/2006 | Schnitzer |
| 7,098,871 B1 | 8/2006 | Tegreene et al. |
| 7,102,817 B1 | 9/2006 | Wu |
| 7,153,299 B1 | 12/2006 | Tu et al. |
| 7,165,552 B2 | 1/2007 | Deem et al. |
| 7,166,537 B2 | 1/2007 | Jacobsen et al. |
| 7,167,317 B2 | 1/2007 | Jung et al. |
| 7,186,251 B2 | 3/2007 | Malecki et al. |
| 7,218,822 B2 | 5/2007 | Treado et al. |
| 7,221,388 B2 | 5/2007 | Sudo et al. |
| 7,234,816 B2 | 6/2007 | Bruzzone et al. |
| 7,247,847 B2 | 7/2007 | Webb et al. |
| 7,304,310 B1 | 12/2007 | Shortt et al. |
| 7,393,321 B2 * | 7/2008 | Doguchi et al. ............ 600/109 |
| 7,420,675 B2 * | 9/2008 | Giakos ............ 356/364 |
| 7,433,552 B2 * | 10/2008 | Kiesel et al. ............ 385/12 |
| 7,591,780 B2 | 9/2009 | Jacobsen et al. |
| 7,629,659 B2 | 12/2009 | Jacobsen et al. |
| 7,823,215 B2 * | 10/2010 | Giakos ............ 850/31 |
| 7,835,074 B2 | 11/2010 | Jacobsen et al. |
| 7,842,046 B1 | 11/2010 | Nakao |
| 7,901,870 B1 * | 3/2011 | Wach ............ 430/321 |
| 8,358,462 B2 | 1/2013 | Jacobsen |
| 2001/0007051 A1 | 7/2001 | Nakashima |
| 2001/0007511 A1 | 7/2001 | Minami et al. |
| 2001/0012053 A1 | 8/2001 | Nakamura |
| 2001/0024848 A1 | 9/2001 | Nakamura |
| 2001/0049509 A1 | 12/2001 | Sekine et al. |
| 2002/0007110 A1 | 1/2002 | Irion |
| 2002/0034537 A1 | 3/2002 | Schulze et al. |
| 2002/0039594 A1 | 4/2002 | Unger |
| 2002/0080248 A1 | 6/2002 | Adair et al. |
| 2002/0111534 A1 | 8/2002 | Suzuki et al. |
| 2002/0166946 A1 | 11/2002 | Iizuka |
| 2002/0168776 A1 | 11/2002 | Cizdziel et al. |
| 2002/0188204 A1 | 12/2002 | McNamara |
| 2002/0193660 A1 | 12/2002 | Weber |
| 2003/0071342 A1 | 4/2003 | Honda et al. |

(56) References Cited

U.S. PATENT DOCUMENTS

| | | | |
|---|---|---|---|
| 2003/0092995 A1 | 5/2003 | Thompson | |
| 2003/0114732 A1 | 6/2003 | Webler et al. | |
| 2003/0197812 A1* | 10/2003 | Hirata et al. | 348/744 |
| 2003/0199761 A1 | 10/2003 | Yock | |
| 2003/0202127 A1* | 10/2003 | Hirata et al. | 348/744 |
| 2003/0208211 A1* | 11/2003 | Kortenbach | 606/151 |
| 2003/0220574 A1* | 11/2003 | Markus et al. | 600/466 |
| 2003/0222325 A1* | 12/2003 | Jacobsen et al. | 257/432 |
| 2004/0006274 A1 | 1/2004 | Giller et al. | |
| 2004/0015049 A1 | 1/2004 | Zaar | |
| 2004/0017961 A1 | 1/2004 | Petersen et al. | |
| 2004/0059204 A1 | 3/2004 | Marshall | |
| 2004/0097788 A1 | 5/2004 | Mourlas et al. | |
| 2004/0097804 A1 | 5/2004 | Sobe | |
| 2004/0111031 A1 | 6/2004 | Alfano et al. | |
| 2004/0115955 A1 | 6/2004 | Motoyama et al. | |
| 2004/0165858 A1* | 8/2004 | Curatolo | 385/147 |
| 2004/0181148 A1 | 9/2004 | Uchiyama et al. | |
| 2004/0222031 A1* | 11/2004 | Szalony et al. | 180/311 |
| 2004/0225222 A1 | 11/2004 | Zeng et al. | |
| 2004/0257566 A1 | 12/2004 | Chism | |
| 2004/0260148 A1* | 12/2004 | Schnitzer | 600/108 |
| 2005/0004453 A1 | 1/2005 | Tearney et al. | |
| 2005/0054902 A1 | 3/2005 | Konno | |
| 2005/0065504 A1 | 3/2005 | Melsky et al. | |
| 2005/0084229 A1 | 4/2005 | Babbitt et al. | |
| 2005/0088576 A1* | 4/2005 | Hirata et al. | 348/781 |
| 2005/0099824 A1 | 5/2005 | Dowling et al. | |
| 2005/0110892 A1* | 5/2005 | Yun | 348/354 |
| 2005/0124875 A1 | 6/2005 | Kawano et al. | |
| 2005/0152421 A1 | 7/2005 | Fujitani | |
| 2005/0154277 A1 | 7/2005 | Tang et al. | |
| 2005/0158899 A1* | 7/2005 | Jacobsen et al. | 438/29 |
| 2005/0171521 A1 | 8/2005 | Brucker et al. | |
| 2005/0174649 A1 | 8/2005 | Okada et al. | |
| 2005/0187568 A1 | 8/2005 | Klenk et al. | |
| 2005/0226636 A1 | 10/2005 | Hiramatsu et al. | |
| 2005/0231718 A1 | 10/2005 | Goodall et al. | |
| 2005/0234345 A1 | 10/2005 | Yang | |
| 2005/0264813 A1* | 12/2005 | Giakos | 356/369 |
| 2005/0267340 A1 | 12/2005 | Ishihara et al. | |
| 2005/0288555 A1 | 12/2005 | Binmoeller | |
| 2006/0009682 A1 | 1/2006 | Nagasawa et al. | |
| 2006/0013593 A1 | 1/2006 | Yokoo et al. | |
| 2006/0017928 A1 | 1/2006 | Crowther | |
| 2006/0051036 A1 | 3/2006 | Treado et al. | |
| 2006/0069312 A1 | 3/2006 | O'Connor | |
| 2006/0079835 A1 | 4/2006 | Frassica | |
| 2006/0106283 A1 | 5/2006 | Wallace et al. | |
| 2006/0135921 A1 | 6/2006 | Wiercinski et al. | |
| 2006/0142700 A1 | 6/2006 | Sobelman et al. | |
| 2006/0146172 A1 | 7/2006 | Jacobsen et al. | |
| 2006/0161048 A1 | 7/2006 | Squicciarini | |
| 2006/0181774 A1 | 8/2006 | Ojima et al. | |
| 2006/0253088 A1 | 11/2006 | Chow et al. | |
| 2007/0010709 A1 | 1/2007 | Reinschke | |
| 2007/0032796 A1 | 2/2007 | Chin-Chen et al. | |
| 2007/0066869 A1 | 3/2007 | Hoffman | |
| 2007/0073321 A1 | 3/2007 | Mikkaichi et al. | |
| 2007/0083232 A1 | 4/2007 | Lee | |
| 2007/0088276 A1 | 4/2007 | Stubbs et al. | |
| 2007/0135803 A1 | 6/2007 | Belson | |
| 2007/0146887 A1 | 6/2007 | Ikeda et al. | |
| 2007/0228300 A1 | 10/2007 | Smith | |
| 2007/0233187 A1 | 10/2007 | Lobello | |
| 2007/0239066 A1 | 10/2007 | Laham et al. | |
| 2007/0255392 A1 | 11/2007 | Johnson | |
| 2008/0045794 A1 | 2/2008 | Belson | |
| 2008/0058601 A1 | 3/2008 | Fujimori | |
| 2008/0071141 A1 | 3/2008 | Gattani et al. | |
| 2008/0094326 A1 | 4/2008 | Yamaki et al. | |
| 2008/0114309 A1 | 5/2008 | Zuckerman | |
| 2008/0143822 A1 | 6/2008 | Wang et al. | |
| 2008/0160257 A1 | 7/2008 | Takada et al. | |
| 2008/0177141 A1 | 7/2008 | Wu et al. | |
| 2008/0183080 A1 | 7/2008 | Abraham | |
| 2008/0188767 A1 | 8/2008 | Oaki et al. | |
| 2008/0227893 A1 | 9/2008 | Tamori et al. | |
| 2008/0267562 A1 | 10/2008 | Wang et al. | |
| 2009/0027765 A1 | 1/2009 | Kamijima | |
| 2009/0036764 A1 | 2/2009 | Rivas et al. | |
| 2009/0054791 A1 | 2/2009 | Flusberg | |
| 2009/0082626 A1 | 3/2009 | Ichimura et al. | |
| 2009/0119808 A1* | 5/2009 | Giakos | 850/31 |
| 2009/0137928 A1 | 5/2009 | Quick et al. | |
| 2009/0143645 A1 | 6/2009 | Matthes | |
| 2009/0155371 A1 | 6/2009 | Sojka et al. | |
| 2009/0156899 A1 | 6/2009 | Konishi | |
| 2009/0180197 A1 | 7/2009 | Jacobsen | |
| 2009/0213894 A1* | 8/2009 | Grapov et al. | 372/107 |
| 2009/0234325 A1 | 9/2009 | Rozenberg et al. | |
| 2009/0267270 A1 | 10/2009 | Murakami et al. | |
| 2009/0287048 A1 | 11/2009 | Jacobson et al. | |
| 2009/0306474 A1 | 12/2009 | Wilson | |
| 2009/0326321 A1 | 12/2009 | Jacobsen | |
| 2010/0016662 A1 | 1/2010 | Salsman et al. | |
| 2010/0085567 A1 | 4/2010 | Dottery et al. | |
| 2010/0106134 A1 | 4/2010 | Jolly et al. | |
| 2010/0134872 A1 | 6/2010 | Johnson et al. | |
| 2010/0171821 A1 | 7/2010 | Jacobsen et al. | |
| 2010/0188492 A1 | 7/2010 | Jacobsen et al. | |
| 2010/0248178 A1 | 9/2010 | Nahlieli | |
| 2011/0137117 A1 | 6/2011 | Jacobsen et al. | |
| 2011/0204265 A1 | 8/2011 | Smith et al. | |
| 2011/0242302 A1 | 10/2011 | Jacobsen et al. | |
| 2011/0245765 A1 | 10/2011 | Jacobsen et al. | |
| 2011/0251456 A1 | 10/2011 | Jacobsen et al. | |
| 2011/0270277 A1 | 11/2011 | Jacobsen et al. | |

FOREIGN PATENT DOCUMENTS

| | | |
|---|---|---|
| DE | 19859434 | 7/2000 |
| EP | 0482997 | 4/1992 |
| EP | 0550 995 | 7/1993 |
| EP | 0639043 | 2/1995 |
| EP | 0681809 | 11/1995 |
| EP | 1104182 | 5/2001 |
| EP | 1195130 | 4/2002 |
| EP | 1477104 | 11/2004 |
| EP | 1488737 | 12/2004 |
| EP | 1626436 | 2/2006 |
| EP | 1647569 | 4/2006 |
| EP | 1880656 | 1/2008 |
| JP | 58-046924 | 3/1983 |
| JP | 63-155115 | 6/1988 |
| JP | H01282514 | 11/1989 |
| JP | H05-039501 | 2/1993 |
| JP | 5 -049602 | 3/1993 |
| JP | H05197828 | 8/1993 |
| JP | H07-148105 | 6/1995 |
| JP | H07-222712 | 8/1995 |
| JP | 08-076028 | 3/1996 |
| JP | 08084700 | 4/1996 |
| JP | H09-021963 | 1/1997 |
| JP | 11 137512 | 5/1999 |
| JP | 2001/314365 | 11/2001 |
| JP | 2004004929 | 1/2004 |
| JP | 2004-086553 | 3/2004 |
| JP | 2004094873 | 3/2004 |
| JP | 2004/329700 | 11/2004 |
| JP | 2005334462 | 8/2005 |
| JP | 2006/162418 | 6/2006 |
| JP | 2006/320369 | 11/2006 |
| JP | 2007-167387 | 7/2007 |
| JP | 2007/312290 | 11/2007 |
| JP | 2009-367946 | 4/2009 |
| KR | 10-2008-027935 | 3/2008 |
| WO | WO 98/38907 | 9/1998 |
| WO | WO 99/40624 | 8/1999 |
| WO | WO 00/54033 | 9/2000 |

(56) References Cited

FOREIGN PATENT DOCUMENTS

| WO | WO 03/081831 | 10/2003 |
|---|---|---|
| WO | WO 2006/060777 | 6/2006 |
| WO | WO 2007/138889 | 12/2007 |

OTHER PUBLICATIONS

Boppart, S.A. et al., "Optical imaging technology in minimally invasive surgery," Surg. Endosc., 1999, vol. 13, pp. 718-722.
Frequency; Wikipedia, The Free Encyclopedia; http://en.wikipedia.org/wiki/Frequency; as accessed May 9, 2008; 4 pages.
Fujimoto, "High resolution in vivo (2001) o intra-arterial imaging with optical-coherence tomography"; Heart 1999; 82:128-133.
Gaoping et al.; Research on the Measurement of Grin Lens Focused Spot Diameter and Resolution; Applied Optics; 1995; vol. 16, No. 6.
Gradient Index (GRIN) Lenses; Grin Tech; 2 pages.
Harder et al; Against the Migraine; Science News Online; http://www.sciencenews.org/articles/20050219/bob8.asp; Feb. 19, 2005; 11 pages.
http://news.thomasnet.com/fullstory/23462, "*Near-IR Camera Utilizes CCD Array with Phosphor Coating*"; Jun. 11, 2003; 5 pages.
Introduction to Gradient Index Optics; http://grintech.de/e_main_grin.htm; as accessed May 1, 2008; 7 pages.
Johansson et al.; "Generation of Turquoise Light by Sum Frequency Mixing of a Diode-Pumped Solid-State Laser and a Laser Diode in Periodically Poled KTP," Optics Express; Oct. 4, 2004; pp. 4935-4940; vol. 12, No. 12.
Knittel, "Endoscope-compatible confocal microscope using a gradient index-lens system," Optics Communications 188 (2001) 267-273.
Literature from GRIN TECH, "In vivo medical confocal imaging and optical coherence tomography," www.grintech.de, Revision Jun. 2001, pp. 1-3.
MICROCAM, MINAST Project 5.04, Nov. 11, 1999, http://www.imt.unine.ch/ESPLAB/www/projects/Microcam/, pp. 1-16.
Nguyen, Clark, "Communications Applications of Microelectromechanical Systems," Proceedings, Sensors Expo, May 19-21, 1998, San Jose, CA. pp. 447-455.
Obreja et al.; "Poly (vinyl-alcohol) Films for Microphotonics"; 2004, IEEE, pp. 1-4.
Shape Memory Polymers—Biodegradable Sutures; http://www.azom.com/details.asp?ArticieID=1542; as accessed Nov. 6, 2007; 4 pages.
Surgical Needles for Use With Sutures; Wikipedia, The Free Encyclopedia; as accessed Nov. 6, 2007; 6 pages.
Tearney, G.J. et al., "Scanning single-mode fiber optic catheter-endoscope for optical coherence tomography," Optics Letters, Apr. 1, 1996, vol. 21, No. 7, pp. 543-545.
Tsuchida et al. "Design of Imaging Lens Systems that Use Low Dispersive Radial Gradient-Index Rod," Jpn.J.Appl.Phys.vol. 37 (1998) pp. 3633-3637.
Xie et al; GRIN Lens Rod Based Probe for Endoscopic Spectral Domain Optical Coherence Tomography with Fast Dynamic Focus Tracking; Optics Express; Apr. 17, 2006; 9 pages; vol. 14, No. 8.
Xuting Technologies Co., Ltd.; http://www.xutingby.com/en/products/glinfo.htrn; as accessed May 1, 2008; 5 pages.
Zeis, Michael et al., "Color Business Report," ISSN 1055-3339. Jul. 2002, p. 5.
Subrahmanyam et al; Lens Aberrations; A Text Book of Optics; Jan. 1, 2004; Chapter 9, pp. 199-200; ; S. Chand & Co. Ltd.
Office action for U.S. Appl. No. 12/896,731 dated Sep. 2, 2015, 14 pages.
Office Action for U.S. Appl. No. 13/966,030 dated Aug. 6, 2015, 28 pages.
Office action for U.S. Appl. No. 14/248,184 dated Sep. 11, 2015, 19 pages.

* cited by examiner

METHOD AND DEVICE FOR INCREMENTAL WAVELENGTH VARIATION TO ANALYZE TISSUE

CLAIM OF PRIORITY

This application is a continuation of U.S. patent application Ser. No. 12/512,188 which claims priority to U.S. Provisional Application No. 61/084,755 filed on Jul. 30, 2008, both of which are incorporated herein by reference in their entireties.

RELATED CASES

The present invention is related to co-pending U.S. patent application Ser. Nos. 10/391,489; 10/391,490; 11/810,702; 10/391,513; 11/292,902; and 12/079,741 and U.S. Pat. No. 7,166,537 all of which are incorporated herein by reference in their entireties.

FIELD OF THE INVENTION

The present invention relates to the field of miniaturized imaging devices. More specifically it relates to a device having a light source capable of propagating a predetermined wavelength of light onto a target and a lens system configured to receive light reflected from the target.

BACKGROUND

Minimally invasive diagnostic medical procedures are used to assess the interior surfaces of an organ by inserting a tube into the body. The instruments utilized may have a rigid or flexible tube and provide an image for visual inspection and photography, but also enable taking biopsies and retrieval of foreign objects. Analysis of image data collected during the inspection and imaging of the interior of the body cavity is a critical component of proper diagnosis of disease and other related conditions.

In geometrical optics, a focus, also called an image point, is the point where light rays originating from a point on the object converge. An image, or image point or region, is in focus if light from object points is converged almost as much as possible in the image, and out of focus if light is not well converged. A principal focus or focal point is a special focus. For a lens, or a spherical or parabolic mirror, it is a point onto which collimated light parallel to the axis is focused. The distance in air from the lens or mirror's principal plane to the focus is called the focal length.

When a lens (such as a photographic lens) is set to "infinity", its rear nodal point is separated from the sensor or film, at the focal plane, by the lens' focal length. Objects far away from the camera then produce sharp images on the sensor or film, which is also at the image plane. Photographers sometimes refer to the image plane as the focal plane; these planes coincide when the object is at infinity, but for closer objects the focal plane is fixed, relative to the lens, and the image plane moves, by the standard optical definitions.

Generally speaking, to render objects in focus, the lens must be adjusted to increase the distance between the rear nodal point and the film, to put the film at the image plane. The focal length f, the distance from the front nodal point to the object to photograph or image $S_1$, and the distance from the rear nodal point to the image plane $S_2$ are then related by:

$$\frac{1}{S_1} + \frac{1}{S_2} = \frac{1}{f}$$

As $S_1$ is decreased, $S_2$ must be increased. For example, consider a normal lens for a 35 mm camera with a focal length of f=50 mm. To focus a distant object ($S_1 \approx \infty$) the rear nodal point of the lens must be located a distance $S_2$=50 mm from the image plane. To focus an object 1 m away ($S_1$=1000 mm), the lens must be moved 2.6 mm further away from the image plane, to $S_2$=52.6 mm.

SUMMARY OF THE INVENTION

It has been recognized that it would be advantageous to develop an improved miniaturized micro-camera catheter device capable of analyzing tissues without the need to physically move a lens system with respect to the tissue and/or with respect to an image sensor.

According to one embodiment of the present invention, as broadly described and claimed herein, the present invention features a method of imaging a desired target using a miniaturized imaging device. The method comprises providing a miniaturized imaging device comprising a lens system and an imaging array, wherein the distance from a distal end of the lens system to the imaging array is fixed. The method further comprises advancing the miniaturized imaging device near the desired target and determining a distance from a distal end of the lens system to the desired target. The method further comprises calculating a desired wavelength of light based on the determined distance from the distal end of the lens system to the desired target and propagating the desired wavelength of light onto the target. The method also comprises receiving the desired wavelength of light reflected off of the target.

In accordance with another embodiment, the present invention further features a method of imaging a target within a cavity using a miniaturized imaging device comprising providing a miniaturized imaging device having a stationary lens system and an imaging array, wherein the distance from a distal end of each of the stationary lens systems to the imaging array is fixed. The method further comprises advancing the miniaturized imaging device within a cavity and propagating a starting wavelength of light onto the target within the cavity. The method further comprises receiving the starting wavelength of light reflected from the target onto the imaging array and incrementally adjusting the starting wavelength of light to a different wavelength of light. The method further comprises propagating the different wavelength of light onto the target within the cavity and receiving the different wavelength of light reflected from the target onto the imaging array. The method further comprises determining an optimal wavelength of light for imaging an object in focus.

In accordance with an additional embodiment, the present invention also resides in a miniaturized imaging device disposed on a distal end of a catheter, comprising at least one imaging array disposed on a distal end of the catheter and a plurality of lens systems disposed on the at least one imaging array, wherein the distance from a distal end of the stationary lens system to the at least one imaging array is fixed, wherein each of the plurality of lens systems has a different longitudinal length. A light source is disposed on a distal end of the catheter and is adapted to propagate a starting monochromatic wavelength of light onto a target and incrementally adjust the starting monochromatic wavelength of light to a different monochromatic wavelength of light. In one aspect of the invention, the plurality of lens systems comprises a plurality of GRIN lenses.

In accordance with an additional embodiment, the present invention also resides in an imaging array disposed on a distal end of the catheter and a plurality of lens systems disposed on the imaging array, wherein the distance from a distal end of the stationary lens system to the imaging array is fixed. The plurality of lens systems are configured substantially parallel to one another and the distance from a front surface of each of the plurality of lens systems to the target is different.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

DETAILED DESCRIPTION OF EXAMPLE EMBODIMENT(S)

Figure 1:
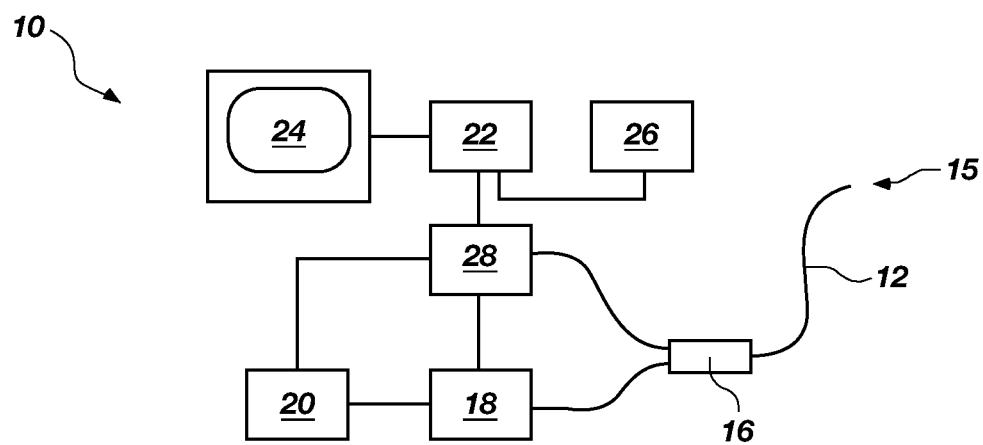
FIG. 1 is an exemplary view of a medical imaging system in accordance with an embodiment of the present invention.

Reference will now be made to, among other things, the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

It must be noted that, as used in this specification and the appended claims, singular forms of "a," "an," and "the" include plural referents unless the context clearly dictates otherwise.

An "SSID," "solid state imaging device," or "SSID chip" in the exemplary embodiments generally comprises an imaging array or pixel array for gathering image data, and can further comprise conductive pads electrically coupled to the imaging array, which facilitates electrical communication therebetween. In one embodiment, the SSID can comprise a silicon chip substrate or other semiconductor chip substrate (e.g., InGaAs) or amorphous silicon thin film transistors (TFT) having features typically manufactured therein. The SSID can also comprise a non-semiconductor chip substrate treated with a semiconductor material. Features can include the imaging array, the conductive pads, metal traces, circuitry, etc. Other integrated circuit components can also be present for desired applications. However, it is not required that all of these components be present, as long as there is a means of gathering visual or photon data, and a means of sending that data to provide a visual image or image reconstruction.

The term "umbilical" can include the collection of utilities that operate the SSID or the micro-camera as a whole. Typically, an umbilical includes a conductive line, such as electrical wire(s) or other conductors, for providing power, ground, clock signal, and output signal with respect to the SSID, though not all of these are strictly required. For example, ground can be provided by another means than through an electrical wire, e.g., to a camera housing such as micromachined tubing, etc. The umbilical can also include other utilities such as a light source, temperature sensors, force sensors, fluid irrigation or aspiration members, pressure sensors, fiber optics, microforceps, material retrieval tools, drug delivery devices, radiation emitting devices, laser diodes, electric cauterizers, and electric stimulators, for example. Other utilities will also be apparent to those skilled in the art and are thus comprehended by this disclosure.

"GRIN lens" or "graduated refractive index lens" refers to a specialized lens that has a refractive index that is varied radially from a center optical axis to the outer diameter of the lens. In one embodiment, such a lens can be configured in a cylindrical shape, with the optical axis extending from a first flat end to a second flat end. Thus, because of the differing refractive index in a radial direction from the optical axis, a lens of this shape can simulate the effects of a more traditionally shaped lens.

With these definitions in mind, reference will now be made to, among other things, the accompanying drawings, which illustrate, by way of example, embodiments of the invention.

As noted above, to capture an image that is in focus, efforts must be made to ensure that for a lens system with a given focal length f, the distance from the front nodal point of a lens system to the object to image $S_1$ (the object plane), and the distance from the rear nodal point to the image plane $S_2$ are related by:

$$\frac{1}{S_1} + \frac{1}{S_2} = \frac{1}{f}$$

As $S_1$ is decreased, $S_2$ must be increased. For older image capturing systems (e.g., photographic cameras) wherein the lens system was fixed with respect to the image plane (e.g., the film), in order to capture an image in focus, the distance from the object to be photographed and the lens system had to be fixed. With advancements in technology, lens systems could be used within the camera to adjust the distance from the lens system to the image plane, thereby allowing the respective movement needed to capture an image in focus to happen within the camera itself. However, it is important to note that this type of movement becomes increasingly more difficult and much less reliable when operating imaging systems at the microscopic scale. Accordingly, the present invention resides in a method and device for capturing an image in focus with a miniaturized imaging system, without having to physically adjust the distance from the lens system of the imaging device with respect to the image plane and/or the object plane.

For purposes of discussion, for a thick lens (one which has a non-negligible thickness), or an imaging system consisting of several lenses and/or mirrors (e.g., a photographic lens or a telescope), the focal length is often called the effective focal length (EFL), to distinguish it from other commonly-used parameters; front focal length (FFL) or front focal distance (FFD) (the distance from the front focal point of the system to the vertex of the first optical surface) and back focal length (BFL) or back focal distance (BFD) (the distance from the vertex of the last optical surface of the system to the rear focal point). For an optical system in air, the effective focal length gives the distance from the front and rear principal planes to the corresponding focal points. If the surrounding medium is not air, then the distance is multiplied by the refractive index of the medium. In general, the focal length or EFL is the value that describes the ability of the optical system to focus light, and is the value used to calculate the magnification of the system. The other parameters are used in determining where an image will be formed for a given object position. For the case of a lens of thickness d in air, and surfaces with radii of curvature $R_1$ and $R_2$, the effective focal length f is given by:

$$\frac{1}{f} = (n-1)\left[\frac{1}{R_1} - \frac{1}{R_2} + \frac{(n-1)d}{nR_1 R_2}\right],$$

where n is the refractive index of the lens medium. The quantity 1/f is also known as the optical power of the lens.

The corresponding front focal distance is:

$$FFD = f\left(1 + \frac{(n-1)d}{nR_2}\right),$$

and the back focal distance:

$$BFD = f\left(1 - \frac{(n-1)d}{nR_1}\right).$$

As will be recognized by one skilled in the art, as noted above, in standard lens systems, focal length can generally be thought of as the distance from a point within the lens system to the focal plane when the lens is imaging an object at infinity. The term working distance is thought of as the distance from an end of the lens system (e.g., a distal end) to the focal plane. While the working distance and the focal length are different, they share the location of the focal plane in common. For a GRIN lens, the geometrical gradient constant "g" and the lens length "z" determine the focal length "f" and the working distance "s" of the lens as represented below where "n" represents the refractive index of the lens at the center of the lens profile:

$$s = \frac{1}{ng\tan(gz)},$$

$$f = \frac{1}{ng\sin(gz)}.$$

Micro-Camera Device

Turning to the drawings, in which like reference numerals represent like or corresponding elements in the drawings, in one embodiment of the present invention, FIG. 1 illustrates a medical imaging system 10 comprising a micro-catheter 12 having an imaging device disposed at a distal tip 15 of the micro-catheter 12. A processor 22, such as an appropriately programmed computer, is provided to control the imaging system 10 and create an image of anatomy adjacent the distal tip portion 15, within a patient (not shown), displayable on a monitor 24, and storable in a data storage device 26. An interface 28 is provided which supplies power to the imaging device 14 and feeds a digital image signal to the processor based on a signal received from the imaging device via an electrical umbilical, including conductive wires through the micro-catheter 12. A light source may also be provided at the distal end of the micro-catheter 12. In one aspect, the system further includes a fitting 16 enabling an imaging fluid, such as a clear saline solution, to be dispensed to the distal tip portion of the micro-catheter 12 from a reservoir 18 through an elongated tubular member removably attached to the micro-catheter 12 or through a lumen of the micro-catheter 12 to displace body fluids as needed to provide a clearer image. Fluids may be pumped to the distal end of the micro-catheter for other reasons described herein. A pump 20 is provided, and is manually actuated by a medical practitioner performing a medical imaging procedure, or can be automated and electronically controlled so as to dispense fluid on demand according to control signals from the practitioner, sensors, or according to software commands.

Figure 2:
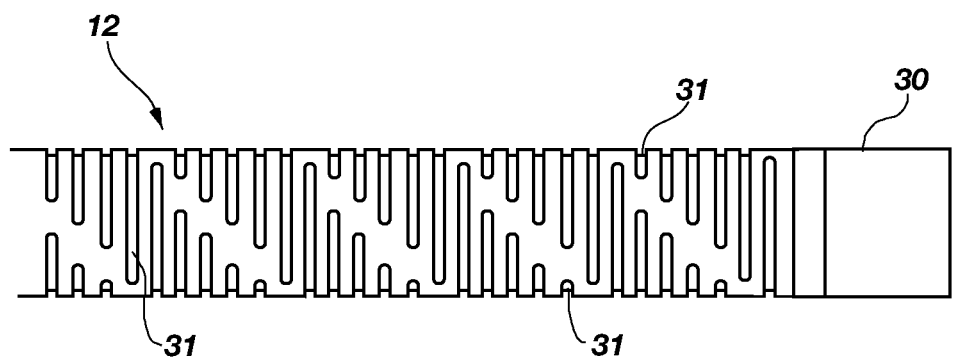
FIG. 2 is a side view of a micro-catheter in accordance with one embodiment of the present invention.
Figure 3:
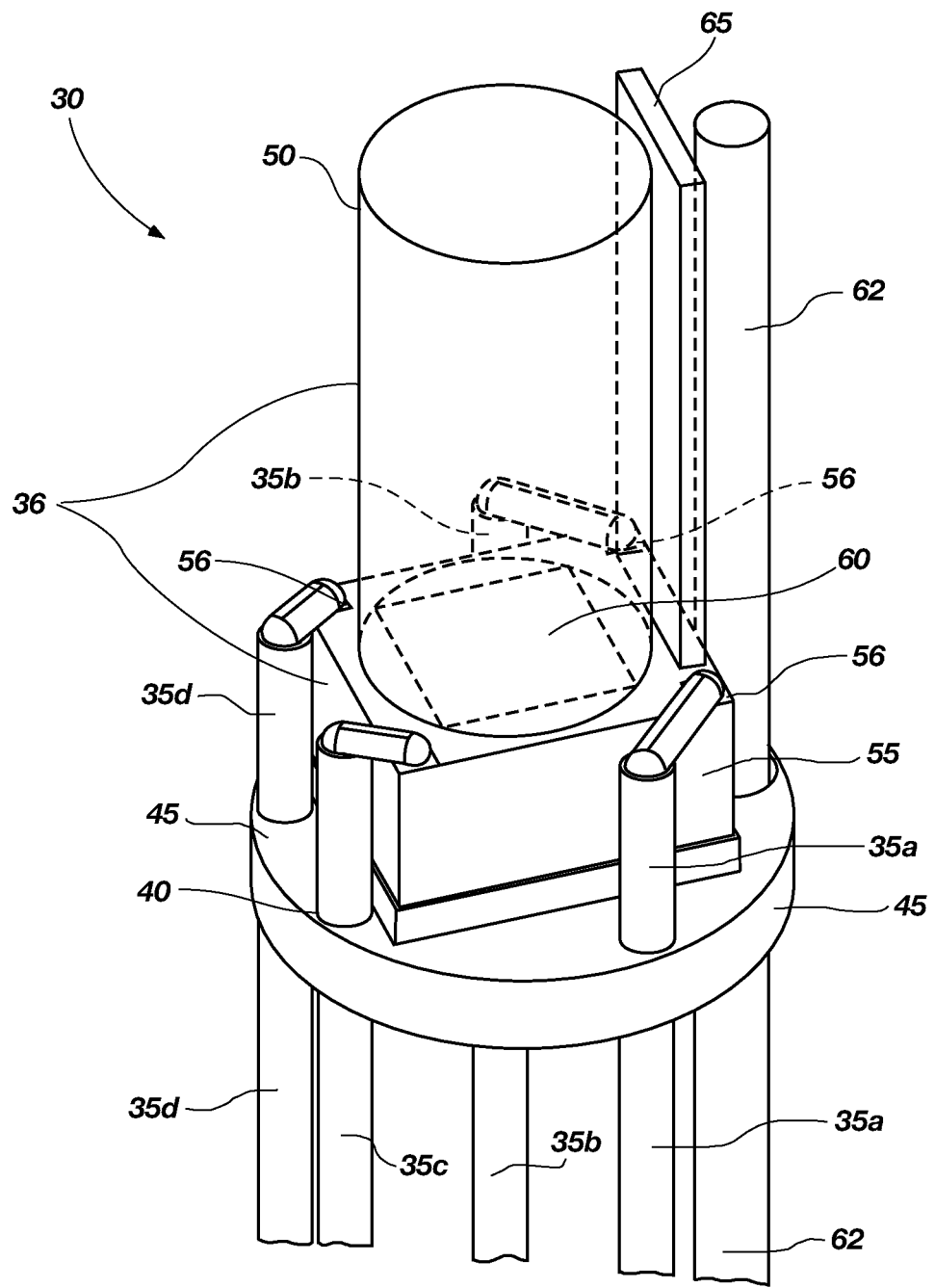
FIG. 3 is a perspective view of an imaging structure according to one embodiment of the present invention.

With reference now to FIGS. 2 and 3, according to one embodiment of the present invention, an imaging device 30 is disposed on a distal end of a micro-catheter 12. Micro-machined cuts 13 are disposed non parallel to a longitudinal direction of the micro-catheter 12 to enable a user, such as a medical practitioner, to guide and steer the distal end of the micro-catheter 12 within a cavity of a patient. In one aspect of the present invention, the micro-catheter may incorporate structure and principles of operation from a catheter disclosed in U.S. Pat. No. 6,014,919 to Jacobsen et al., which is incorporated herein by reference.

In one aspect of the invention, imaging device 30 comprises at least two conductive wires 35a, 35b for conducting electronic image data to the data processor 22 and for securing an imaging structure 36 between the at least two conductive wires 35a, 35b. As illustrated in FIG. 3 however, a plurality of conductive wires 35a, 35b, 35c, 35d may be utilized. The at least two conductive wires 35a, 35b are oriented along a longitudinal axis of the imaging structure 36 and are disposed within alignment apertures 40 of a planar support member 45. The planar support member 45 comprises at least two alignment apertures 40 disposed on opposing sides of the planar support member 45. The alignment apertures 40 are configured to receive and align the at least two conductive wires 35a, 35b along the longitudinal axis of the imaging structure 36. The imaging structure 36 is at least partially secured between the at least two conductive wires 35a, 35b and is disposed adjacent a top surface of the planar support member 45. In one aspect of the invention, the imaging structure 36 comprises a GRIN lens 50 optically coupled to a SSID 55 and disposed adjacent the SSID 55. The GRIN lens 50 is stationary with respect to the SSID and the imaging array. The imaging structure further comprises an imaging array 60 disposed on a top surface of the SSID 55. In one embodiment, the GRIN lens 50 is positioned directly on top of the imaging array 60 of the SSID 55.

The at least two conductive wires 35a, 35b are operatively coupled to the imaging structure 36 and are configured to align the imaging structure 36 therebetween. In one aspect, the conductive wires 35a, 35b are bonded to the imaging structure 36 at contact points 56 disposed on the periphery of a top surface of the SSID 55. In yet another embodiment, the conductive wires 35a, 35b are bonded to a side surface of the SSID 55.

In one embodiment, the alignment apertures 40 are oriented perpendicular to the top surface of the planar support member 45. However, the alignment apertures may also be disposed in any orientation which is not non-parallel to the planar support member 45 as required to optimally align the imaging structure 36 as desired. In one embodiment, the imaging structure is mounted and aligned such that the image plane of the imaging structure 36 is non parallel to a longitudinal axis of the micro-catheter 12. In one aspect of the invention, a light source (e.g., a fiber optic member, LED, etc.) 62 is disposed within an aperture of the planar support member 45 to provide light for imaging. In yet another aspect of the present invention, the imaging structure 36 may incorporate structure and principles of operation from an imaging device disclosed in U.S. Pat. No. 7,166,537 to Jacobsen et al., which is incorporated herein by reference.

Figure 4:
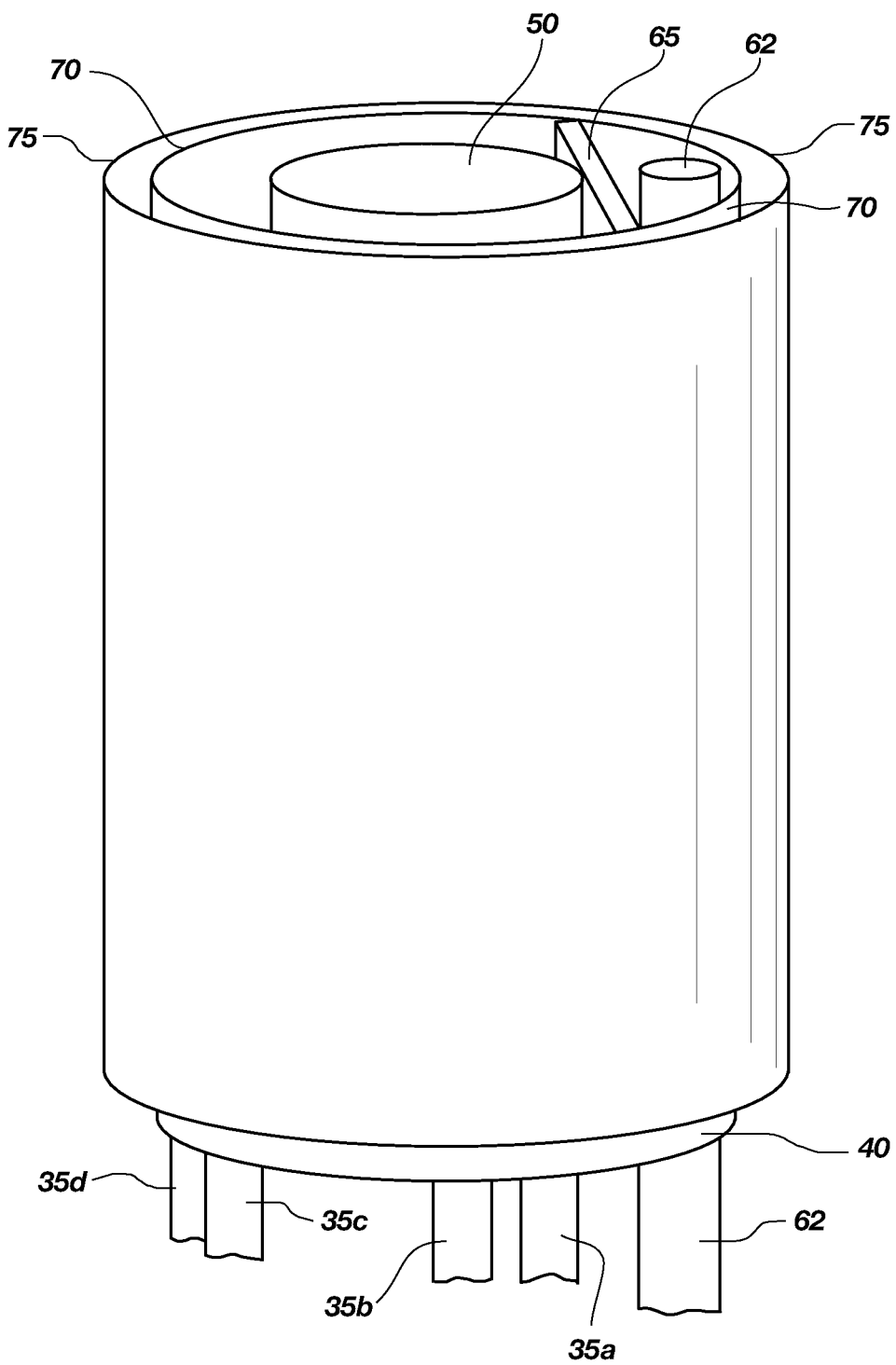
FIG. 4 is a perspective view of an imaging structure according to one embodiment of the present invention.

Referring now to FIGS. 3 and 4, the imaging device 30 further comprises a light blocking member 65. In one aspect, the light blocking member 65 is bonded to a top surface of the SSID 55. In another aspect, the light blocking member 65 is bonded to a side surface of the SSID 55. In yet another aspect, the light blocking member 65 is bonded to a top surface of the planar support member 40. In any event, the light blocking member 65 is oriented adjacent a side surface of the GRIN lens 50 to prevent stray light from the light source entering the side of the GRIN lens. In one aspect, the light blocking member 65 also serves to stabilize and align the GRIN lens 50 on the SSID 55.

In an additional aspect of the invention, a first sleeve member 70 is disposed about the imaging structure 36. An adhesive is disposed within the first sleeve member 70 securing the components of the imaging structure 36 in place as well as securing the first sleeve member 70 to the imaging structure 36. In an additional embodiment, a second sleeve member 75 is disposed about the first sleeve member 70 and secured with an adhesive. In one aspect of the invention, the second sleeve member 75 comprises an opaque material to eliminate secondary light from impacting image quality.

While reference has been made specifically herein to a single GRIN lens 50 used in connection with a SSID 55, it is understood and contemplated herein that a plurality of GRIN lens (not shown) could be used with a plurality of SSIDs (not shown). In one aspect, each of the single GRIN lens/SSID pairs is provided with a filter media designed to pass and reflect different wavelengths of light. Advantageously, each GRIN lens/SSID pair would receive light reflected from the same target but would receive different wavelengths of light reflected from the target. A composite image could be created from the plurality of imaging devices receiving different wavelengths of light reflected from the same target. In another aspect, an optimal image may be selected from each of the GRIN lens/SSID pairs and utilized for display of the target area.

Figure 5:
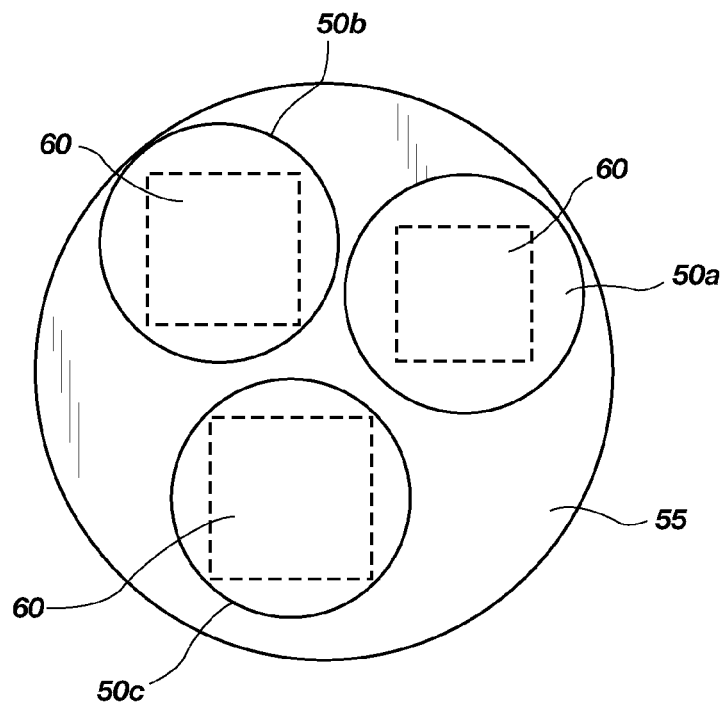
FIG. 5 is a top view of an imaging structure having a plurality of GRIN lenses in accordance with one embodiment of the present invention.
Figure 6:
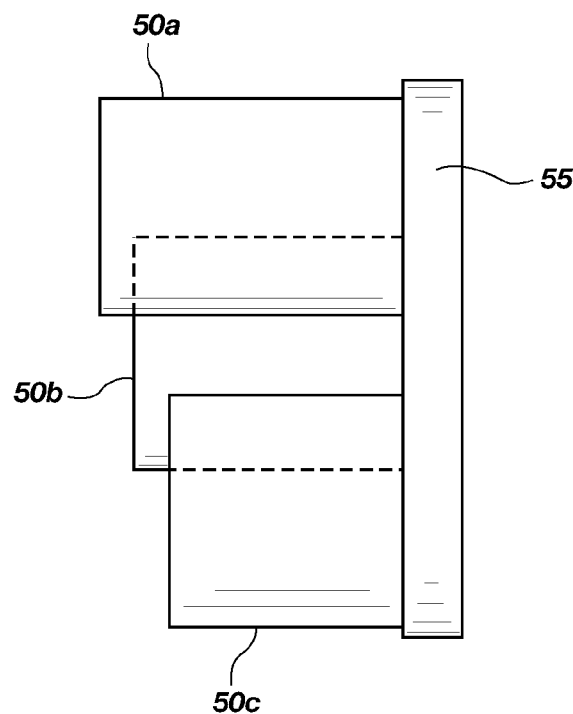
FIG. 6 is a side view of the imaging structure of FIG. 5.

With reference now to FIGS. 5 and 6, in accordance with one embodiment of the present invention, a miniaturized imaging device is disclosed. As with the other miniaturized imaging devices discussed herein, the device is adapted to be disposed on a distal end of a catheter. The device comprises at least one imaging array 60 disposed on a SSID 55, however, a plurality of imaging arrays 60 are shown. A plurality of GRIN lenses 50a, 50b, 50c are disposed on the imaging arrays 60. In this aspect, the distance from a distal end of the GRIN lenses 50a, 50b, 50c to the imaging arrays 60 is fixed and each of the GRIN lenses 50a, 50b, 50c has a different longitudinal length. As such, the working distance (and focal length) of each of the GRIN lenses is also different.

In one aspect of the invention, the back focal length of the plurality of GRIN lens is approximately zero for a predetermined monochromatic wavelength of light. In this manner, the GRIN lenses 50a, 50b, 50c can be disposed directly in contact with the imaging arrays 60 and a rear plane of each of the plurality of GRIN lenses can be substantially coplanar. While not shown on FIGS. 5 and 6, a light source may be disposed on a distal end of the catheter and can be configured to propagate a starting monochromatic wavelength of light onto a target and incrementally adjust the starting monochromatic wavelength of light to a different monochromatic wavelength of light. For example, the light source may be adapted to propagate light at 550 nanometers and thereafter increase or decrease the wavelength of light in 10 nanometer increments, 100 nanometer increments, or other increments as suits a particular application. The amount of the increment and the timing of the increment may be manually adjusted by the user and/or may be set to adjust automatically as suits a particular application.

Figure 7:
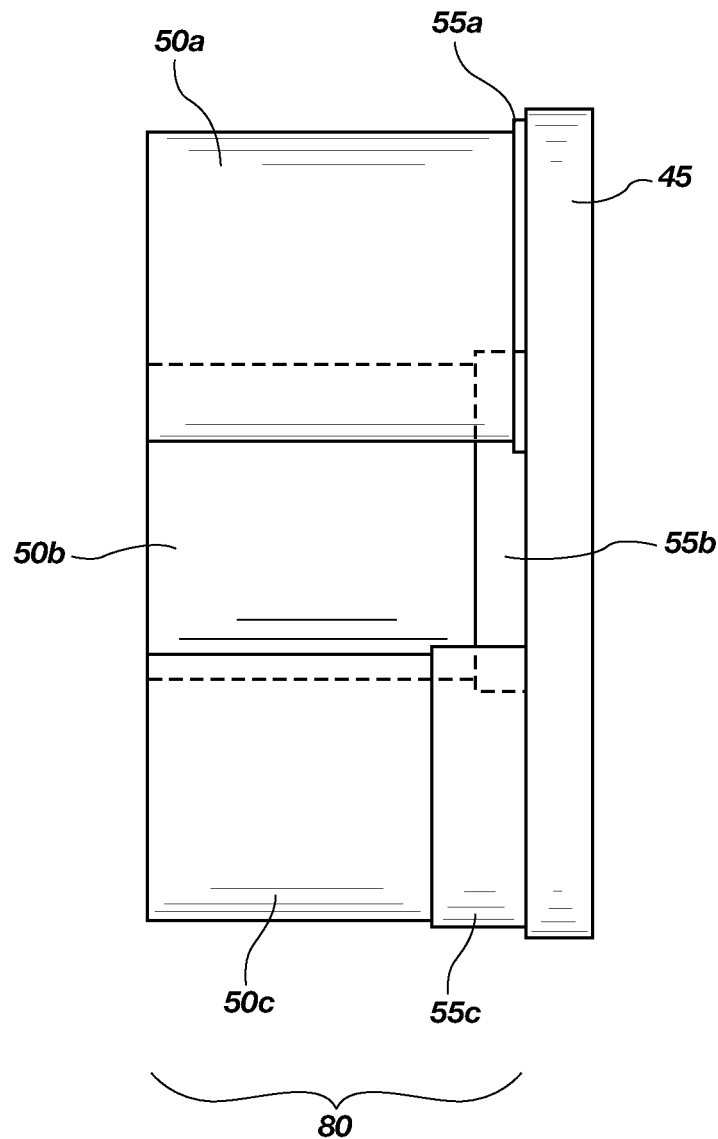
FIG. 7 is a side view of an imaging structure having a plurality of GRIN lenses in accordance with one embodiment of the present invention.

In accordance with an additional embodiment of the present invention, as illustrated on FIG. 7, a plurality of GRIN lens/SSID pairs 80 are disposed on a planar guide member 45. A longitudinal length of each of the GRIN lenses is different. In this manner, because each GRIN lens has a different length, the respective working distance of each of the GRIN lenses is also different. As shown, the SSIDs 55a, 55b, 55c of each of the GRIN lens/SSID pairs have a different longitudinal length. The longitudinal length of each of the SSID's is configured such that the distal end of each of the GRIN lenses 50a, 50b, 50c are substantially coplanar.

Method of Operation

In optics, chromatic aberration is caused by a lens having a different refractive index for different wavelengths of light (the dispersion of the lens). Longitudinal and lateral chromatic aberration of a lens is seen as "fringes" of color around the image, because each color in the optical spectrum cannot be focused at a single common point on the optical axis. As the focal length of a lens system is dependent on its specific geometry and configuration, different wavelengths of light will be focused on different positions. That is, for a single lens system with a fixed geometry and fixed relative to an image plane, different wavelengths of light reflected from an object to an image plane will not each be in focus.

As noted and as is known in the art, different wavelengths of light reflected from an object and passing through a lens system converge at different points. It is with this principle in mind that particular embodiments of the present invention are directed. For a particular lens system having an object a determined distance away from the distal end of the lens system, an optimal wavelength of light exists for achieving optimal focus of the image on the image plane. For example, for a GRIN lens, such as a Grintech IRFL-035-005 the working distance is 5 mm. For a target object that is 5 mm away from the distal end of said GRIN lens, an optimal wavelength of light for capturing an image that is in focus is thought to be approximately 550 nm when used in embodiments of the imaging system described herein. That is, for the specific GRIN lens noted above, light at a wavelength of approximately 550 nm which is reflected from an object 5 mm away from the distal end of the GRIN lens is thought to converge at substantially the same point of the rear end of the GRIN lens. In like manner, when a target object is 3 mm away from the distal end of the same GRIN lens system, an optimal wavelength of light for capturing an image that is in focus is thought to be approximately 450 nm. In like manner, when a target object is 10 mm away from the distal end of the same GRIN lens system, an optimal wavelength of light for capturing an image that is in focus is thought to be approximately 650 nm.

Accordingly, in one embodiment of the present invention, a method of imaging a target using a miniaturized imaging device is disclosed comprising providing a miniaturized imaging device having a stationary lens system (such as the GRIN lens system described above) and an imaging array, wherein the distance from the stationary lens system to the imaging array is fixed. The method further comprises advancing the miniaturized imaging device near the desired target and determining a distance from a distal end of the stationary lens system to the desired target. The distance from the distal end of the stationary lens system to the desired target may be calculated by an infrared range calculation device or any other suitable process (e.g., an active autofocus technique discussed in more detail below). The method further comprises calculating a desired wavelength of light based on the determined distance from the distal end of the stationary lens system to the desired target. The desired wavelength of light is propagating onto the target and is received through the lens system. In this manner, the optimal wavelength of light for capturing an image that is in focus may be calculated and utilized as the light source to illuminate the desired target. Advantageously, no movement of the lens system with respect to the image sensor (e.g., SSID) and/or the target to be imaged is required in order to properly capture a focused image of the object. Additionally, as the image is captured using an achromatic source of light, problems associated with chromatic aberration as noted above are not encountered.

In accordance with an additional embodiment of the present invention, a method of imaging a target within a cavity using a miniaturized imaging device is disclosed. The method comprises providing a miniaturized imaging device having a stationary lens system and an imaging array, wherein the distance from the stationary lens system to the imaging array is fixed. In other words, the lens system is stationary with respect to the imaging array. The miniaturized imaging device is advanced within the cavity to a desired location and a starting wavelength of light is propagated onto the target within the cavity. The starting wavelength of light reflected from the target is received onto the imaging array after which the starting wavelength of light is incrementally adjusted to a different wavelength of light. The different wavelength of light is propagated onto the target within the cavity and received onto the imaging array as with the starting wavelength of light.

The incremental adjustments of wavelength may be through frequency and or amplitude variation of the wavelength and may be performed on an as needed basis to determine an optimal wavelength of light based on the focal length of a given lens system and the distance of the object from the distal end of the lens system. That is, in one aspect, as the miniaturized imaging device is advanced within a patient the medical practitioner may wish to stop advancing the imaging device and capture images of a fixed object. In this manner, the incremental adjustments of the wavelength need only be conducted until an optimal wavelength of light is detected. However, if the medical practitioner wishes to image portions of the patient while advancing the imaging device within the patient, the incremental adjustments may be ongoing at a relatively rapid pace. Because the movement of the imaging device within the patient will result in a variation in distances from the distal end of the imaging device to any particular target, a collection of both in focus and out of focus images will be captured by the imaging device and sent to the imaging system processor. However, depending on the particular settings and processes employed by the overall imaging system, only those images which are determined to be in focus would be provided on the system display. In this manner, the medical practitioner may advance the imaging device within a patient and view an in focus image of the patient irrespective of the exact distance from the distal end of the imaging device to a particular target.

In accordance with one aspect of the present invention, the optimal wavelength may be determined using an autofocus technique. The autofocus system (not shown) relies on one or more sensors to determine correct focus. Autofocus systems may be categorized into passive and active systems. An active autofocus system (not shown) measures the distance to the subject independently of the optical system, and subsequently adjusts the optical system (e.g., the wavelength of light propagated onto a target) for correct focus. There are various ways to measure distance with an active autofocus system, including ultrasonic sound waves and infrared light. In the first case, sound waves and/or infrared light is emitted from the imaging device, and by measuring the delay in their reflection, distance to the subject is calculated. Once the distance is calculated, an optimal wavelength of light may be determined for a particular lens system geometry.

Passive autofocus systems determine correct focus by performing passive analysis of the image that is entering the optical system. They generally do not direct any energy, such as ultrasonic sound or infrared light waves, toward the subject. However, an autofocus assist beam of usually infrared light may be required when there is not enough light to take passive measurements. Passive autofocusing can be achieved by phase detection or contrast measurement.

Phase detection is achieved by dividing the incoming light into pairs of images and comparing them. In one aspect, the system uses a beam splitter (implemented as a small semi-transparent area of the main reflex mirror, coupled with a small secondary mirror) to direct light to an autofocus sensor disposed on the imaging device. Two optical prisms capture the light rays coming from the opposite sides of the lens and divert it to the autofocus sensor, creating a simple rangefinder with a base identical to the lens' diameter. The two images are then analyzed for similar light intensity patterns (peaks and valleys) and the phase difference is calculated in order to find if the object is in front focus or back focus position. Contrast measurement is achieved by measuring contrast within a sensor field, through the lens system. The intensity difference between adjacent pixels of the sensor naturally increases with correct image focus. The optical system can thereby be adjusted until the maximum contrast is detected. In this method, autofocus does not involve actual distance measurement.

One example of a passive autofocus embodiment includes use of a SSID that provides input to algorithms that compute the contrast of actual image elements. The SSID is typically a single strip of 100 or 200 pixels. Light from the target hits this strip and the microprocessor looks at the values from each pixel. The imaging systems processor evaluates the difference in intensity among adjacent pixels. If the target is out of focus, adjacent pixels have very similar intensities. As incremental modifications are made to the wavelength of light, the processor again evaluates the difference in intensity between adjacent pixels to see if the intensity increased or decreased. The processor then searches for the point where there is maximum intensity difference between adjacent pixels, wherein the maximum intensity difference between adjacent pixels is the point of best focus.

As described in more detail above, the lens system may comprise a plurality of GRIN lenses each having a different effective focal length. While not necessary, each one of the plurality of GRIN lenses may also be positioned on a different imaging array. In this manner, the number of possible "in focus" images resulting from operation of the imaging device as described herein is expanded thereby giving the imaging device a greater depth of operation. That is, because each of the plurality of GRIN lenses has a different effective focal length, and hence a different depth of field, the overall depth at which the imaging device may return an image that is in focus is enhanced.

While the foregoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A miniaturized imaging device disposed on a distal end of a catheter, comprising:
   at least one imaging array disposed on a distal end of the catheter;
   a lens system disposed on the at least one imaging array;
   a light source disposed on a distal end of the catheter adapted to propagate a starting monochromatic wavelength of light onto a target and incrementally adjust the starting monochromatic wavelength of light over different time intervals to a different monochromatic wavelength of light, wherein (i) the light source is adapted to incrementally adjust the wavelength of light only until an optimum wavelength of light is detected when the catheter is stationary, and (ii) the light source is adapted to continually incrementally adjust the wavelength of light when the catheter is non-stationary; and
   a processor coupled to the imaging array configured to generate an image from the plurality of different monochromatic wavelengths of light reflected from the target and further configured to determine an optimal monochromatic wavelength of light to optimize image focus based on the light reflected from the target.

2. The miniaturized imaging device of claim 1, wherein the lens system comprises a plurality of GRIN lenses.

3. The miniaturized imaging device of claim 2, further comprising a plurality of imaging arrays, wherein each of the plurality of GRIN lenses is disposed in direct contact with a separate imaging array.

4. The miniaturized imaging device of claim 3, wherein the working distance of at least one of the plurality of GRIN lenses is approximately zero for a predetermined monochromatic wavelength of light.

5. The miniaturized imaging device of claim 2, wherein each of the plurality of GRIN lenses has a different effective focal length.

6. The miniaturized imaging device of claim 5, wherein each of the plurality of GRIN lenses comprises a different filter media capable of passing and reflecting different wavelengths of light.

7. The miniaturized imaging device of claim 1, further comprising means for determining the distance from a distal end of the lens system to a target.

8. The miniaturized imaging device of claim 1, wherein the light source is capable of propagating an initial wavelength of light and adjusting the wavelength of light in increments of 10 nanometers.

9. The miniaturized imaging device of claim 1, wherein the light source is capable of propagating an initial wavelength of light and adjusting the wavelength of light in increments of 100 nanometers.

10. A miniaturized imaging device disposed on a distal end of a catheter, comprising:
    at least one imaging array disposed on a distal end of the catheter;
    a plurality of lens systems disposed on the at least one imaging array;
    a light source disposed on a distal end of the catheter adapted to propagate a starting wavelength of light onto a target and incrementally adjust the starting wavelength of light over different time intervals to a different wavelength of light;
    a system capable of measuring the distance from a distal end of the lens system to the target;
    a processor coupled to the imaging array configured to generate a plurality of images from the plurality of different monochromatic wavelengths of light reflected from the target, said plurality of images comprising images that are in focus and out of focus, said processor further configured to determine an optimal wavelength of light to optimize image focus based on the light reflected from the target and to determine image focus; and
    a display system coupled to the processor configured to display only those images comprising wavelengths of light determined to comprise the optimal monochromatic wavelength of light to optimize image focus.

11. The device of claim 10, wherein the distance measure system comprises a passive autofocus system.

12. The device of claim 11, wherein the passive autofocus system uses a phase detection technique.

13. The device of claim 11, wherein the passive autofocus system uses a contrast measurement technique.

14. The device of claim 10, wherein the distance measure system comprises an active autofocus system.

15. The device of claim 14, wherein the active autofocus system uses an infrared signal.

16. A miniaturized imaging device disposed on a distal end of a catheter, comprising:
    at least one imaging array disposed on a distal end of the catheter;
    a stationary GRIN lens system disposed in direct contact with the at least one imaging array;
    a light source disposed on a distal end of the catheter adapted to propagate a starting monochromatic wavelength of light onto a target and incrementally adjust the starting monochromatic wavelength of light over different time intervals to a different monochromatic wavelength of light;
    a processor coupled to the imaging array configured to generate a plurality of images from the plurality of different monochromatic wavelengths of light reflected from the target, said plurality of images comprising images that are in focus and out of focus, said processor further configured to determine an optimal monochromatic wavelength of light to optimize image focus based on the light reflected from the target and to determine image focus; and
    a display system coupled to the processor configured to display only those images comprising wavelengths of light determined to comprise the optimal monochromatic wavelength of light to optimize image focus.

17. The device of claim 16, wherein the stationary GRIN lens system comprises a plurality of GRIN lenses fixed to the imaging array, each GRIN lens having a different longitudinal length.

18. The device of claim 17, further comprising a plurality of GRIN lens systems, each GRIN lens system having a different filter media capable of passing and reflecting different wavelengths of light.

19. The device of claim 18, further comprising a light blocking member disposed between the light source and the GRIN lens system.

20. The device of claim 16, further comprising a plurality of GRIN lenses each having a different longitudinal length, wherein each of the GRIN lenses is disposed atop a different solid state imaging device and each of the GRIN lens solid state imaging device pairs are disposed atop a common planar support member.

* * * * *